(12) United States Patent
Hsieh

(10) Patent No.: US 8,025,797 B2
(45) Date of Patent: Sep. 27, 2011

(54) INTEGRATED SYSTEM FOR A PRESSURIZED FLUID GENERATOR AND VORTEX SEPARATOR

(76) Inventor: Chen Hsieh, Ping dong (TW)

( * ) Notice: Subject to any disclaimer, the term of this patent is extended or adjusted under 35 U.S.C. 154(b) by 536 days.

(21) Appl. No.: 12/202,315

(22) Filed: Aug. 31, 2008

(65) Prior Publication Data

US 2010/0051539 A1    Mar. 4, 2010

(51) Int. Cl.
*B01D 21/26* (2006.01)
(52) U.S. Cl. ............ 210/149; 210/512.3; 422/530; 422/533; 422/117
(58) Field of Classification Search .......... 422/527, 422/533, 530, 117, 109; 210/512.1–512.3, 210/149
See application file for complete search history.

(56) References Cited

U.S. PATENT DOCUMENTS

| | | | | |
|---|---|---|---|---|
| 2,881,126 A | * | 4/1959 | Glinka | 208/417 |
| 3,767,365 A | * | 10/1973 | Beesley | 422/259 |
| 4,422,301 A | * | 12/1983 | Watt et al. | 62/48.2 |

* cited by examiner

*Primary Examiner* — Terry Cecil

(57) ABSTRACT

An integrating system of a pressurized fluid generator and vortex separator comprises a pressurized fluid generator and a vortex separator. The pressurized fluid generator includes a high pressure tank which connects to a fluid storage tank and a pressure indicator through a pressure booster pump. A heating element and a temperature indicating controller are installed in the high pressure tank. The vortex separator is connected to the pressurized fluid generator through transfer pipes. The vortex separator includes a vortex separating tank. The vortex separating tank has an outlet at a bottom side thereof; the outlet is connected to a plurality of collection bottles. A spindle is located in the vortex separating tank and is driven by a driving device. The spindle is installed with a penetrating fluid channel which is connected to a plurality of transfer pipes; each of the transfer pipes is installed with a plurality of electric controlled switches.

5 Claims, 8 Drawing Sheets

INTEGRATED SYSTEM FOR A PRESSURIZED FLUID GENERATOR AND VORTEX SEPARATOR

FIELD OF INVENTION

The present invention relates to an integrated system for a pressurized fluid generator and vortex separator, and in particular to a multi-functional integrated system for a pressurized fluid generator and vortex separator system combining a pressurized fluid generator with a vortex separator that provides multiple functions.

DESCRIPTION OF THE PRIOR ART

Prior art pressurized fluids and their related pressurized fluid generators are based on the principle of generating a pressurized fluid above the critical pressure and temperature of a substance. The pressurized fluid has a particular state which has different solubility, density, diffusion coefficient, and a lower viscosity from a normal fluid and so medical, chemical, foodstuffs, and environmental fields all use these pressurized fluids to achieve certain purposes (such as cell rupturing, crystal cleaning, distillation, extraction, and others).

Taking as an example cell rupturing in medical fields, due to its high diffusion ability, the pressurized fluid diffuses into animal and plant cells through the different cell membranes or cell walls, respectively, and by lowering the pressure in a chamber holding the cells to lower the density of the pressurized fluid in the cells for the purpose of destroying the cell membranes or cell walls, the cells are ruptured.

The prior pressurized fluid mentioned above is capable of achieving typical objectives, but with the example of cell rupturing, the prior art pressurized fluid will destroy all of the cells and cannot achieve selective rupturing to keep needed animal or plant cells. So the prior art pressurized fluid and pressurized fluid generator still have limits and inconveniences.

SUMMARY OF THE PRESENT INVENTION

Accordingly, the primary objective of the present invention is to provide a multi-function integrated system for a pressurized fluid generator and vortex separator.

To achieve the above objectives, the present invention provides an integrated system of a pressurized fluid generator and a vortex separator comprising a pressurized fluid generator and a vortex separator. The pressurized fluid generator includes a high pressure tank which connects to a fluid storage tank and a pressure indicator through a pressure booster pump. A heating element and a temperature indicating controller are installed in the high pressure tank; the vortex separator is connected to the pressurized fluid generator through transfer pipes. The vortex separator includes a vortex separating tank; the vortex separating tank has an outlet at a bottom side thereof. The outlet is connected to a plurality of collection bottles. A spindle is located in the vortex separating tank and is driven by a driving device. The spindle is installed with a penetrating fluid channel which is connected to a plurality of transfer pipes; each of the transfer pipes is installed with a plurality of electric controlled switches.

FIELD OF THE INVENTION

In order that those skilled in the art can further understand the present invention, a description will be provided in the following in details. However, these descriptions and the appended drawings are only used to cause those skilled in the art to understand the objects, features, and characteristics of the present invention, but not to be used to confine the scope and spirit of the present invention defined in the appended claims.

Figure 1:
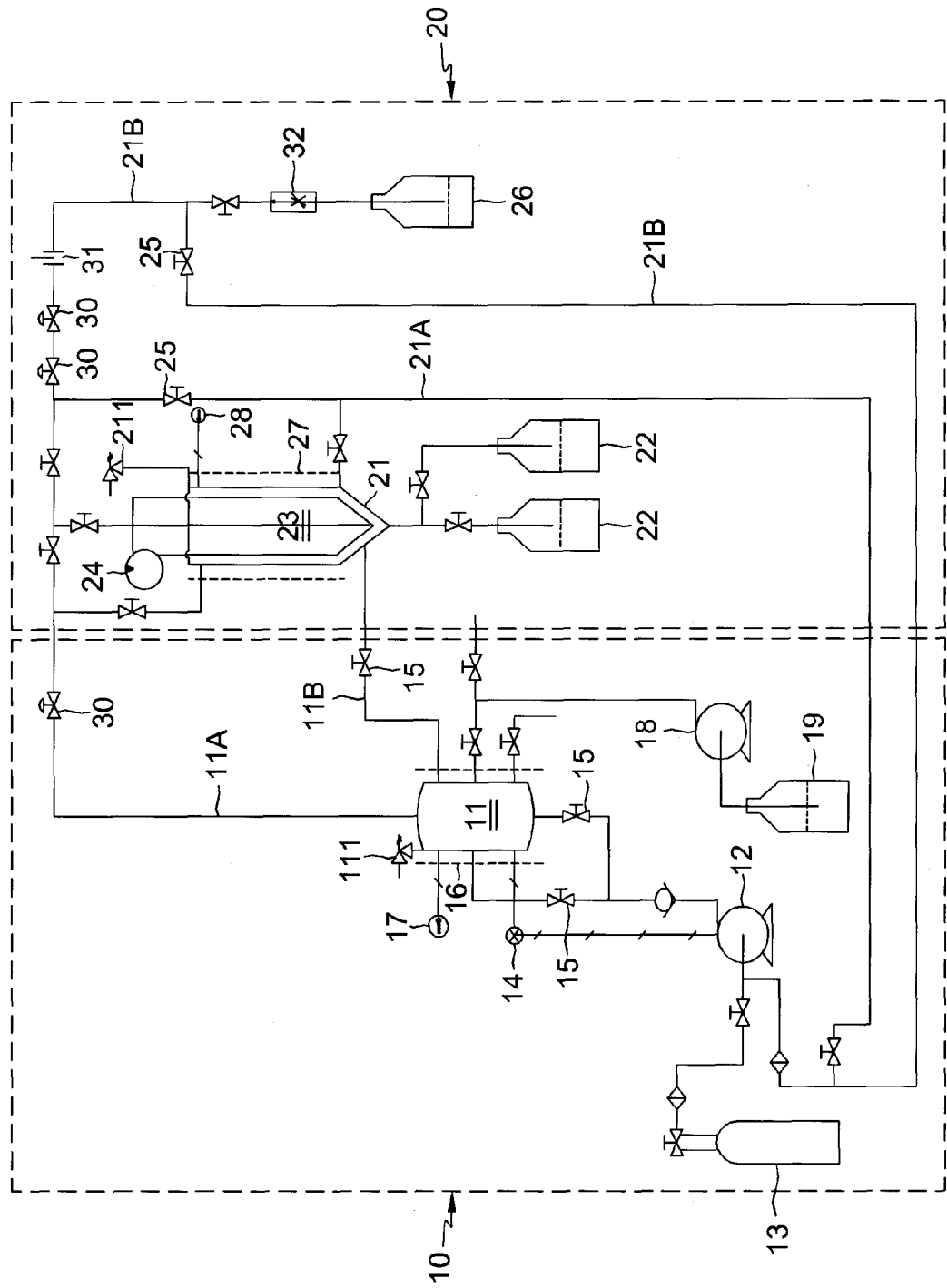
FIG. 1 is a schematic view of the present invention.

With reference to FIG. 1, an integrating system for a pressurized fluid generator and vortex separator includes a pressurized fluid generator 10 and a vortex separator 20.

The pressurized fluid generator 10 (referring to FIG. 1) includes a high pressure tank 11. The high pressure tank 11 is connected to a fluid storage tank 13 and a pressure indicator 14 through a pressure booster pump 12. The fluid tank 13 can store different fluid based on the pressurized fluid to be generated. A plurality of electric controlled switches 15 can be installed between the high pressure tank 11 and the pressure booster pump 12 and between the pressure booster pump 12 and the fluid storage tank 13. A heating element 16 and a temperature indicating controller 17 are installed in the high pressure tank 11. The high pressure tank 11 is heated based on setting temperatures and timing. Furthermore, preferably, the high pressure tank 11 is connected to a co-solvent (or test agent) storage tank 19 through a transfer pump 18.

As illustrated in FIG. 1, the vortex separator 20 is connected to the pressurized fluid generator 10 through the transfer pipes 11A, 11B. The vortex separator includes a vortex separating tank 21. The vortex separating tank 21 has an outlet at a bottom side thereof. The outlet is connected to a plurality of collection bottles 22. A spindle 23 is located in the vortex separating tank 21 and is driven by a driving device 24 (such as a motor) so as to be moved vertically in the vortex separating tank. Further, the spindle 23 is installed with a penetrating fluid channel which is connected to a plurality of transfer pipes 21A, 21B. Preferably, each of the transfer pipes 21A, 21B is installed with a plurality of electric controlled switches 25. The transfer pipe 21B is connected to a plurality of collection bottles 26. Moreover, the vortex separating tank 21 is further installed with a heating element 27 and a temperature controller 28 for heating the vortex separating tank 21 based on setting temperatures and timing.

In a preferable embodiment, the high pressure tank 11 and the vortex separating tank 21 are installed with safety releasing valves 111 and 211 respectively to control the pressure within safe range. While the pressure is above the safe level in the high pressure tank 11 or vortex separating tank 21, the above releasing valves can automatically release pressure for safety.

However, in another preferable embodiment, for controlling pressure and flow in each of the transfer pipes 11A and 21B, a plurality of pressure control valves 30, flow control valves 31, and flow meters 32 are installed thereto, respectively as necessary.

By the structure mentioned above, the pressurized fluid generator and the vortex separator have the following functions.

1. Selective Extraction Cycle Function

Figure 2:
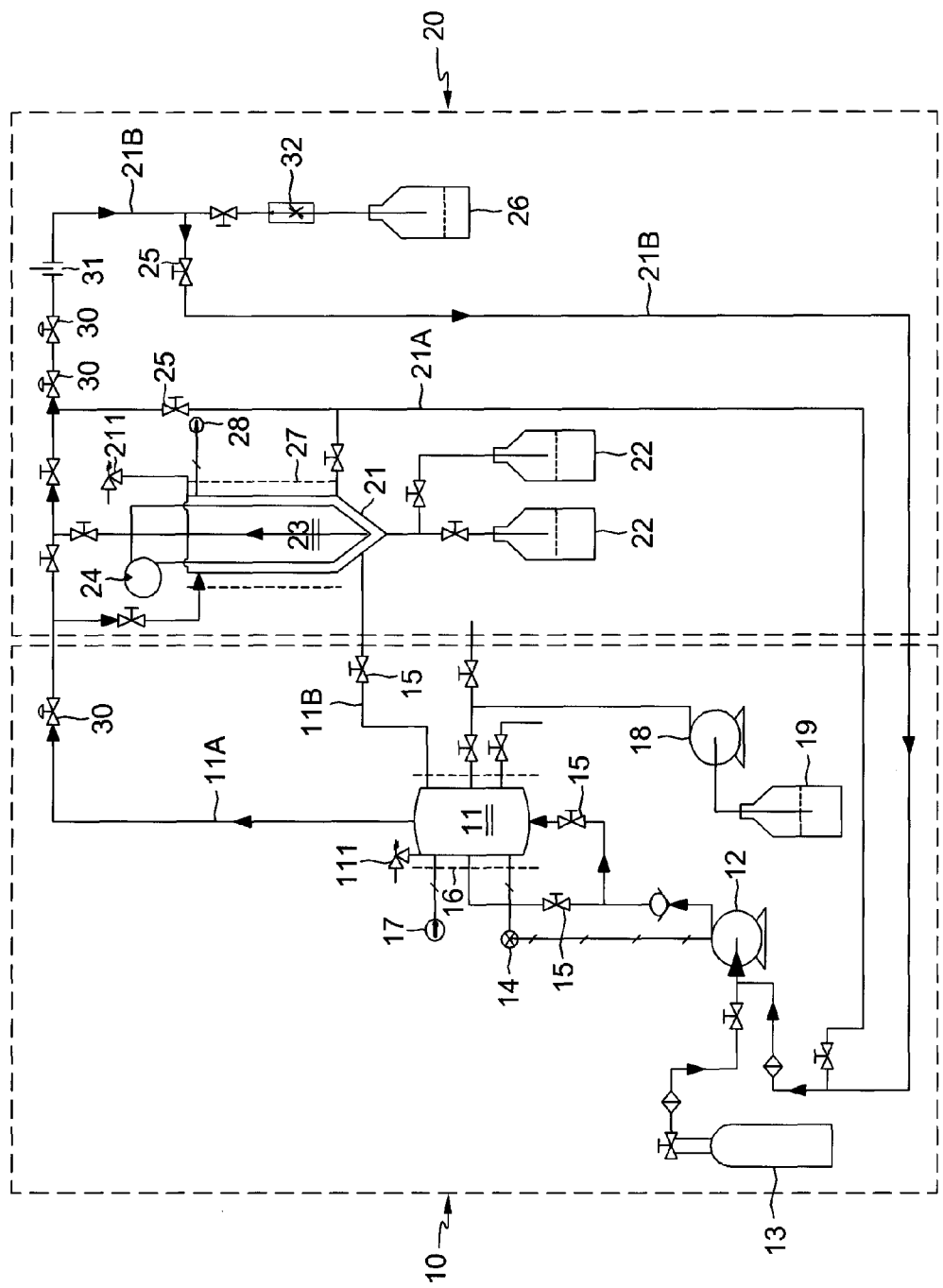
FIG. 2 is a schematic view showing the operation of the selective extraction cycle function of the present invention.
Figure 3:
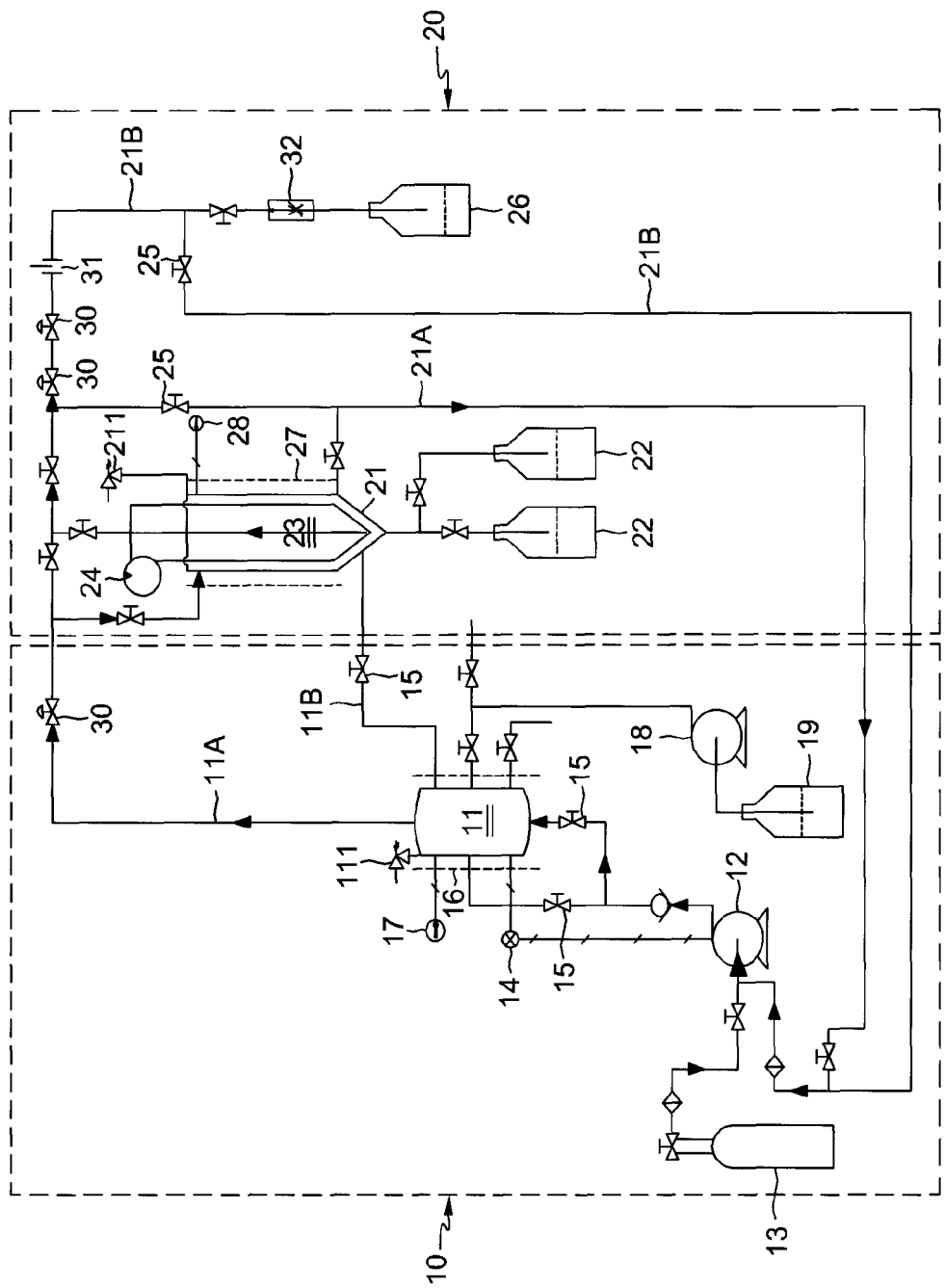
FIG. 3 is another schematic view showing the operation of the selective extraction cycle function of the present invention.

As shown in FIG. 2, the extractives is placed into the high pressure tank 11 and a kind of fluid (such as carbon dioxide) is transferred by the pressure booster pump 12 from the fluid storage tank 13 into the high pressure tank 11. By pressurizing and heating up the high pressure tank 11 through the pressure booster pump 12 and the heating element 27, respectively, the fluid in the tank will become a pressurized fluid highly compatible to the extractives. The pressurized fluid will carry the extractives away from the high pressure tank 11 into the lower-pressure vortex separating tank 21 by connecting the two tanks. Through adjustment of the pressure control valve 30 to stabilize the pressure in the high pressure tank 11 and the vortex separating tank 21 and opening of the fluid channel in the spindle 23 of the vortex separating tank 21, the pressurized fluid will flow back to the high pressure tank 11 through the transfer pipe 21B so that an extraction cycle is achieved. The extract can be collected by the collection bottles 22 and 26, respectively depending on the extraction time needed. The pressurized fluid can flow back to the high pressure tank 11 through the transport pipes 21A to be extracted again, as shown in FIG. 3, and the extract can be directly collected by the collection bottle 22.

2. Selective Batch-Extraction or Continuous-Extraction

Figure 4:
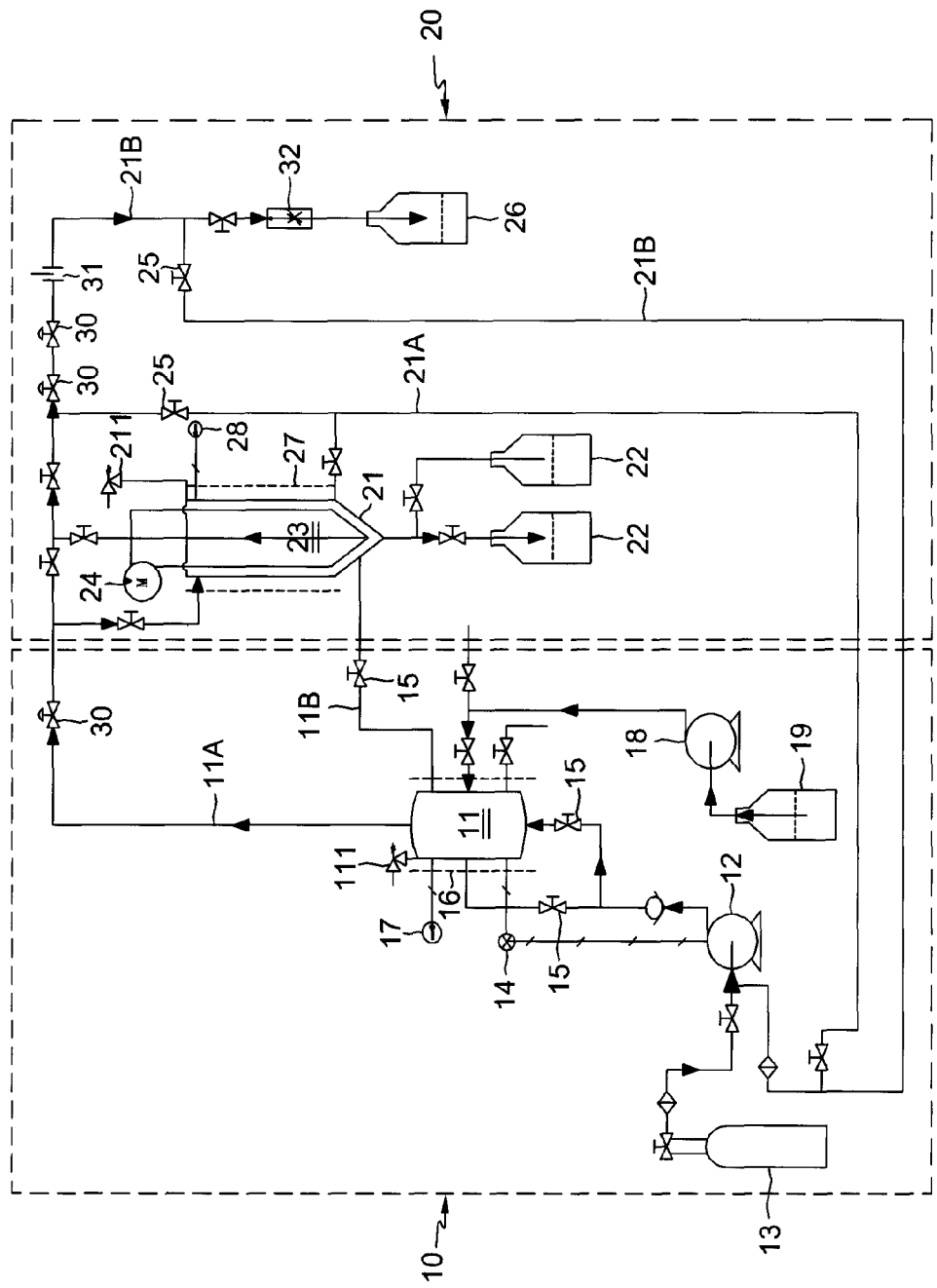
FIG. 4 is a schematic view showing the selective batch-extraction or continuous-extraction of the present invention.

As shown in FIG. 4, the extractives is placed into the high pressure tank 11 and a kind of fluid (such as carbon dioxide) is transferred by the pressure booster pump 12 from the fluid storage tank 13 into the high pressure tank 11. A co-solvent (or a test agent) is transferred into the high pressure tank 11 by the transport pump 18 from the co-solvent (or a test agent) storage tank 19. By pressurizing and heating up the high pressure tank 11 through the pressure booster pump 12 and the heating element 27 respectively, the fluid in the tank will become a pressurized fluid highly compatible to the extractives. The pressurized fluid will carry the extractives away from the high pressure tank 11 into the lower-pressure vortex separating tank 21 by connecting the two tanks. While the pressure is stable between the high pressure tank 11 and the vortex separating tank 21, the collection bottles 22 and 26 can directly collect the extract respectively by opening the fluid channel in the bottom outlet of the spindle 23 of the vortex separating tank 21. The batch-extraction is done and the extract collection is stopped when the pressure in the high pressure tank 11 drops to zero. Or, a continuous-extraction which the extraction and the collection of the extract is sustained can be achieved by maintaining the same pressure and temperature through keeping pressurizing and heating the high pressure tank 11.

3. Crystal Cleaning Function

Figure 5:
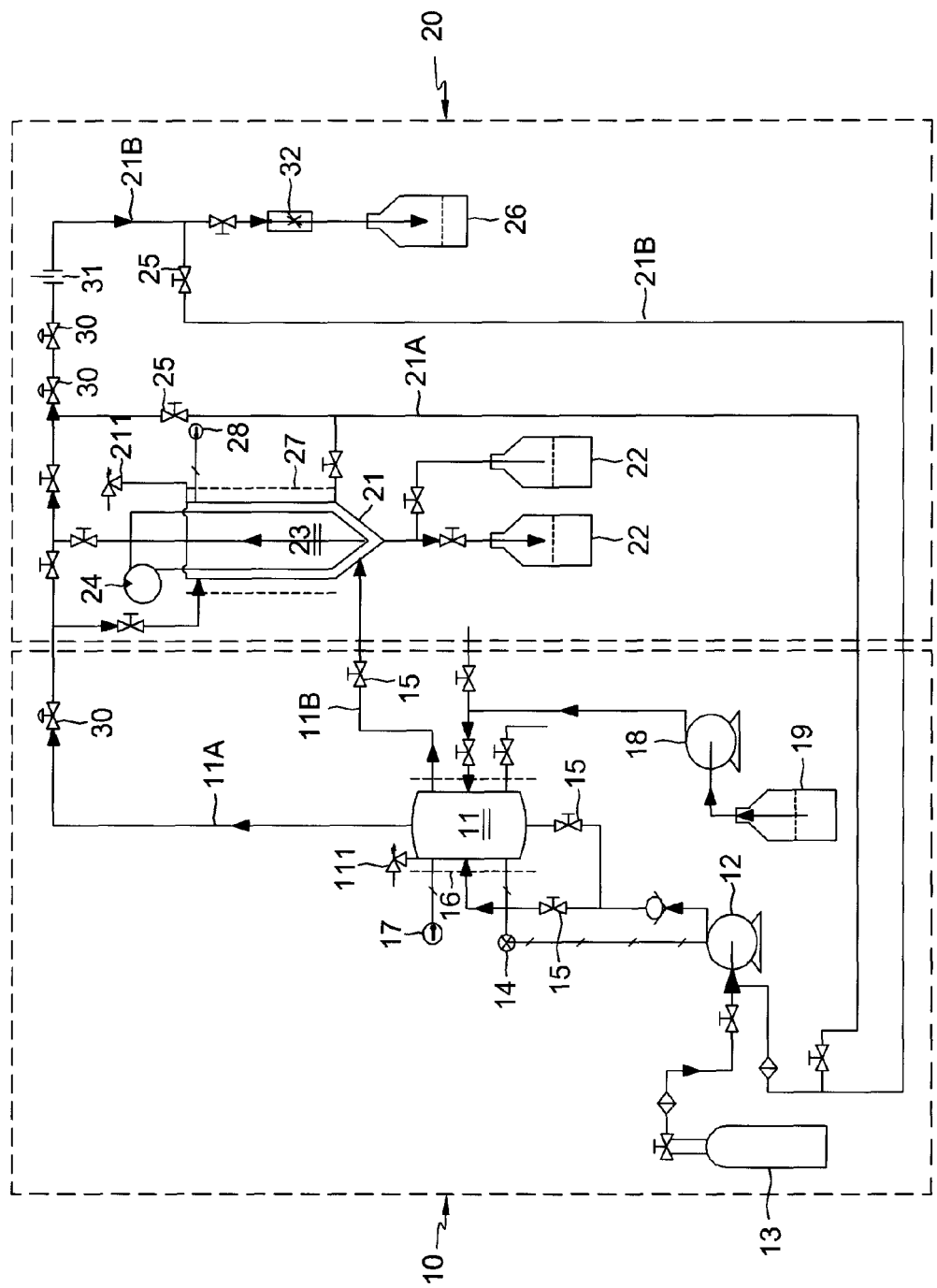
FIG. 5 is a schematic view showing the operation of the crystal cleaning function of the present invention.

As shown in FIG. 5, a crystal which needs to be cleaned is placed into the high pressure tank 11, and the spindle 23 of the vortex separating tank 21 is lowered to the lowest position of the vortex separating tank 21 by the driving device 24. A kind of fluid (such as carbon dioxide) is transported by the pressure booster pump 12 from the fluid storage tank 13 into the high pressure tank 11. A co-solvent (or a test agent) is transferred from the co-solvent (or a test agent) storage tank 19 into the high pressure tank 11 by the transport pump 18. By pressurizing and heating up the high pressure tank 11 through the pressure booster pump 12 and the heating element 27 respectively, the fluid in the tank will become a pressurized fluid so as to raise the cleaning ability of the co-solvent (or a test agent) toward the crystal. The impurity on the crystal will be quickly carried away from the high pressure tank 11 into the lower-pressure vortex separating tank 21 by connecting the two tanks through quickly opening the transfer pipe 11B. While the pressure is stable between the high pressure tank 11 and the vortex separating tank 21, the pressurized fluid and the impurity will be collected by the collection bottles 22 and 26 by opening the fluid channel in the bottom outlet of the spindle 23 of the vortex separating tank 21 so that fast cleaning is achieved. Or, by opening the transfer pipe 11A, and through the transfer pipe 11A the impurity on the crystal will be slowly carried away from the high pressure tank 11 into the lower-pressure vortex separating tank 21. When the pressure is stabilized between the high pressure tank 11 and the vortex separating tank 21, the pressurized fluid and the impurity will be collected by the collection bottles 22 and 26 by opening the fluid channel in the bottom outlet of the spindle 23 of the vortex separating tank 21, so as the slow cleaning capable of keeping the crystal from being scratched is achieved.

4. Selective Germs Destroying and Animal/Plant Cells Explosion Function

Figure 6:
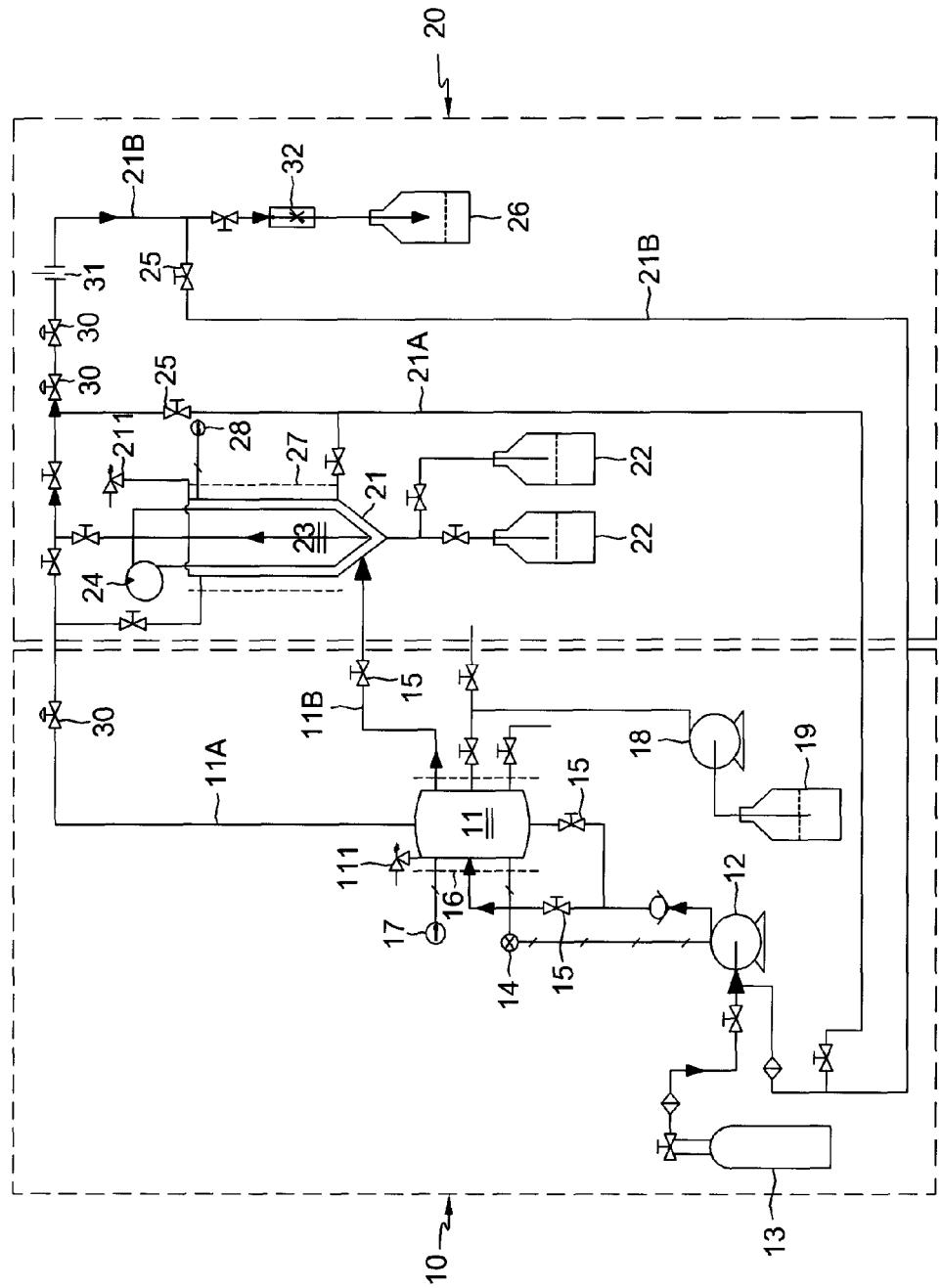
FIG. 6 is a schematic view showing the operation of the selective germ destroying and animal/plant cell explosion function of the present invention.

As shown in FIG. 6, the spindle 23 of the vortex separating tank 21 is lowered to the lowest position of the vortex separating tank 21 by using the driving device 24, and several kinds of germ or animal/plant cells are placed into the high pressure tank 11. A kind of fluid (such as carbon dioxide) is transported by the pressure booster pump 12 from the fluid storage tank 13 into the high pressure tank 11. By pressurizing and heating up the high pressure tank 11 through the pressure booster pump 12 and the heating element 27, respectively, the fluid in the high pressure tank 11 will become a pressurized fluid capable of permeating into the germs or the animal/plant cells. The vortex separating tank 21 will become negative pressure by raising the spindle 23 of the vortex separating tank 21 to a predetermined position in the vortex separating tank 21 by the driving device 24. Through opening the transfer pipe 11B which connects the high pressure tank 11 and the vortex separating tank 21, the pressures between the two tanks are equal. Because of the sudden low pressure, the high pressure tank 11 is under, the pressurized fluid in germs or animal/plant cells will immediately vaporize and in the mean time the cell membranes/walls of the animal/plant cells are destroyed and thus the selective germs destroying and the animal/plant cells explosion is achieved. However, while performing a repeatedly germs destroying or cells explosion, the pressurized fluid can flow back to high pressure tank 11 from the vortex separating tank 21 by lowering the spindle 23 of the vortex separating tank 21 to the lowest position in the vortex separating tank 21 through the driving device 24. After the transfer pipe 11B which connects the high pressure tank 11 and the vortex separating tank 21 is closed, the vortex separating tank 21 will become negative pressure by raising the spindle 23 of the vortex separating tank 21 to the predetermined position in the vortex separating tank 21 through the driving device 24. Again, through quickly opening the transfer pipe 11B which connects the high pressure tank 11 and the vortex separating tank 21, the pressures between the two tanks are equaled. Because of the sudden low pressure the high pressure tank 11 is under, the pressurized fluid in germs or animal/plant cells will immediately vaporize and in the mean time the cell membranes/walls of the animal/ plant cells are destroyed and thus the repeatedly germs destroying and cells explosion is achieved. The vaporized pressurized fluid will be exhausted through transfer pipe 21B by opening the fluid channel.

5. Solute Separation Function

Figure 7:
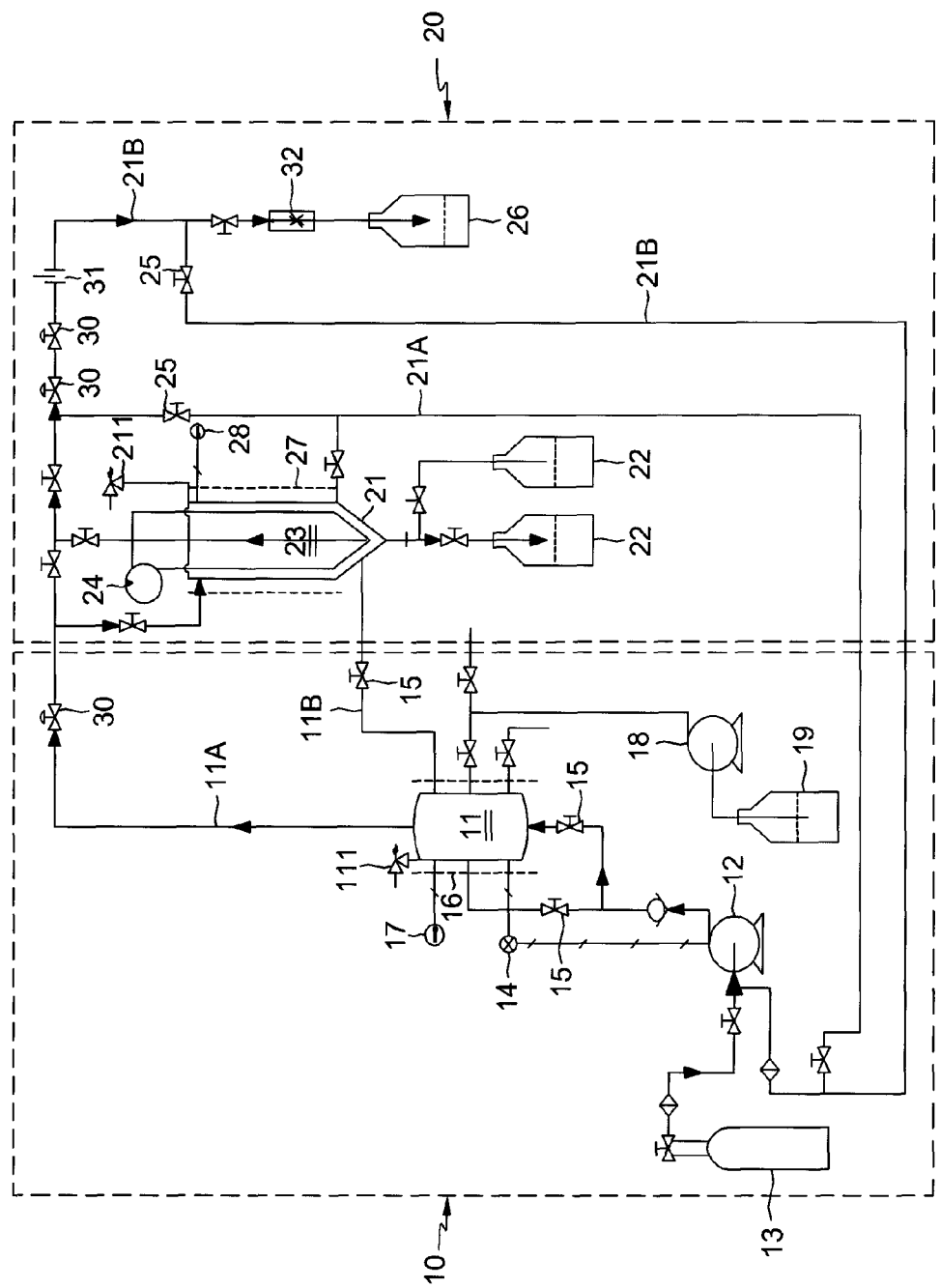
FIG. 7 is a schematic view showing the operation of the solute separation function, the dryer function (or crystallization, distillation, solvent stripping, solvent recycle function), and essence extraction function of the present invention.

The solute separation function can be performed through the high pressure tank 11 and the vortex separating tank 21 separately. The separation through the high pressure tank 11 is shown in FIG. 7. The solution to be separated is placed into the high pressure tank 11, a kind of fluid (such as carbon dioxide) is transferred from the fluid storage tank 13 into the high pressure tank 11 by the pressure booster pump 12. By pressurizing and heating up the high pressure tank 11 through the pressure booster pump 12 and the heating element 27, respectively, the fluid in the high pressure tank 11 will become a pressurized fluid which is highly compatible to the solvent of the solution. Through the lower dielectric constant of the pressurized fluid, the solubility of the solute toward the solvent is lowered. The solute will be separated from the solvent and thus the separation through the high pressure tank 11 is achieved. However, the separation through the vortex separating tank 21 is performed by the high compatibility of the pressurized fluid to the solute and the solvent of the solution. Through connecting the high pressure tank 11 to the vortex separating tank 21 and controlling the temperature and vortex speed, the pressurized fluid and the solvent of the solution will be vaporized and exhausted so that the solute is separated. The separated solute will dash against the wall of the tank and becomes granule so that the separation through the vortex separating tank 21 is achieved.

6. Dryer Function (or Crystallization, Distillation, Solvent Stripping, Solvent Recycle Function)

As shown in FIG. 7, a solution (or a matter) which needs to be dried (or crystallized, distillated, solvent-stripped, or solvent-recycled) is placed in the high pressure tank 11, a fluid (such as carbon dioxide) is transferred from the fluid storage tank 13 into the high pressure tank 11 by the pressure booster pump 12. By pressurizing and heating up the high pressure tank 11 through the pressure booster pump 12 and the heating element 27, respectively, the fluid in the high pressure tank 11 will become a pressurized fluid which is highly compatible to the solvent of the solution. By connecting the high pressure tank 11 to the vortex separating tank 21, the solvent to be removed will be carried away from the high pressure tank 11 into the lower-pressure vortex separating tank 21. The pressurized fluid will be vaporized and exhausted and the solvent will be exhausted from the bottom outlet of the vortex separating tank 21 by controlling the temperature and the vortex speed of the vortex separating tank 21, thus the matter to be dried (or crystallized, distillated, solvent-stripped, or solvent-recycled) will remain in the high pressure tank 11 and be dried so that the Dryer function (or crystallization, distillation, solvent stripping, solvent recycle function) is performed.

7. Essence Extraction Function

As shown in FIG. 7, the matter (such as a peel of an orange, tangerine, or leaves of a rose) from which the essence is to be extracted is placed into the high pressure tank 11, and a kind of fluid (such as carbon dioxide) is transferred from the fluid storage tank 13 into the high pressure tank 11 by the pressure booster pump 12. By pressurizing and heating up the high pressure tank 11 through the pressure booster pump 12 and the heating element 27, respectively, the fluid in the high pressure tank 11 will become a pressurized fluid which is highly compatible to the essence to be extracted. By connecting the high pressure tank 11 to the vortex separating tank 21, the essence needs to be extracted will be carried away from the high pressure tank 11 into the lower-pressure vortex separating tank 21. The pressurized fluid will be vaporized and exhausted by controlling the temperature and the vortex speed of the vortex separating tank 21, and the essence will dash against the wall of the tank and be exhausted from the bottom outlet of the vortex separating tank 21 so as to be collected by the collection bottle 22.

8. Backflow and Recycling Function

Figure 8:
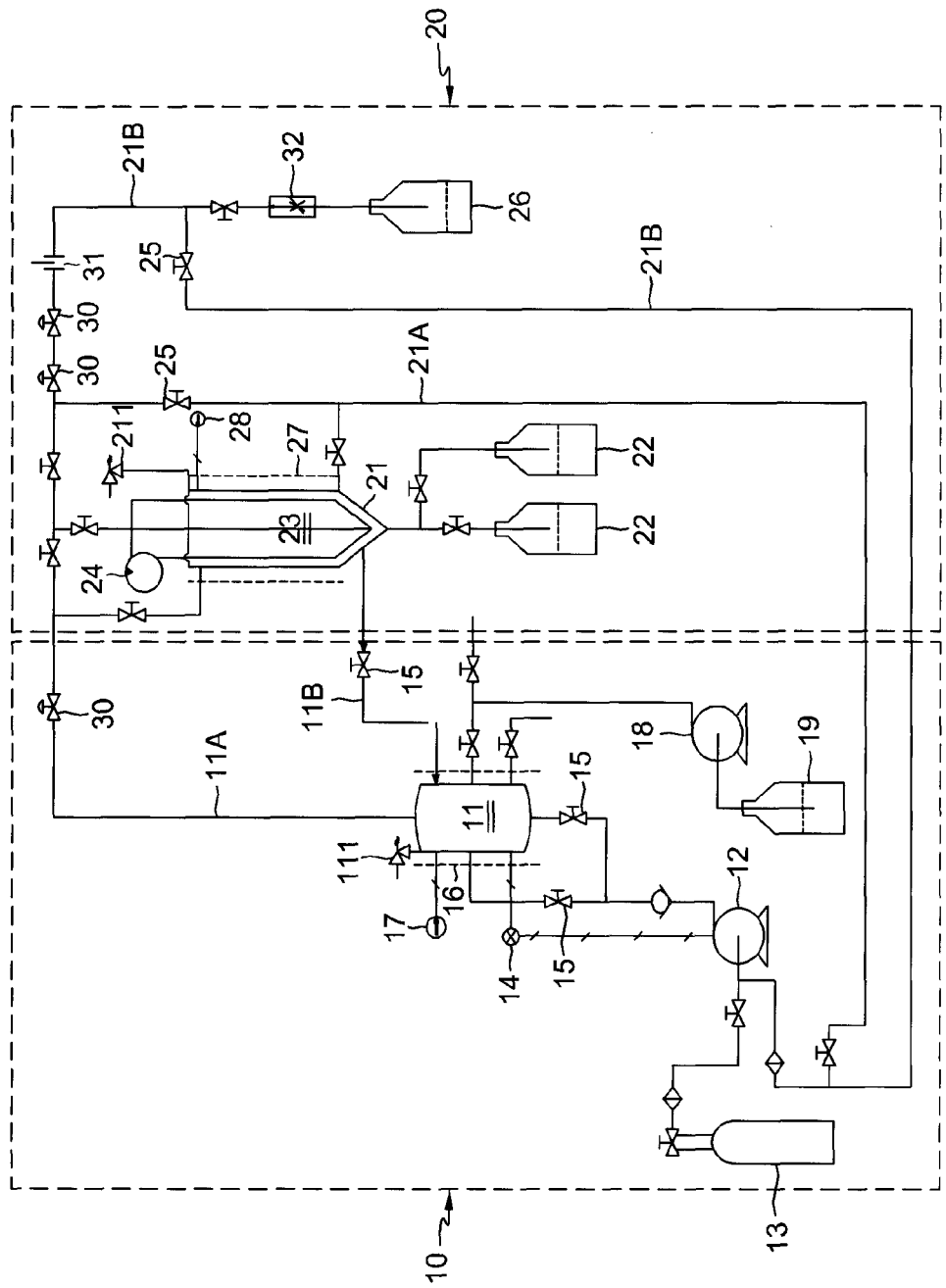
FIG. 8 is a schematic view showing the operation of the backflow and recycling function of the present invention.

About the function of crystal cleaning, the co-solvent (or a test agent) is added to the pressurized fluid in the high pressure tank 11, and also be transferred into the vortex separating tank 21 with the pressurized fluid during the process of crystal cleaning. By the vortex separating tank 21 the pressurized fluid will be vaporized and exhausted and the co-solvent (or test agent) is remained in the high pressure tank 11. As shown in FIG. 8, by lowering the spindle 23 of the vortex separating tank 21 to the lowest position in the vortex separating tank 21 through the driving device 24, the co-solvent can be retrieved and recycled to the high pressure tank 11 through the transfer pipe 11B.

Therefore, through above descriptions and drawings, the present invention with great improvement can provide the selective extraction cycle function, selective batch-extraction or continuous-extraction, crystal cleaning function, selective germs destroying and animal/plant cells explosion function, solute separation function, dryer function (or crystallization, distillation, solvent stripping, solvent recycle function), essence extraction function, and the backflow and recycling function.

The present invention is thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An integrated system of a pressurized fluid generator and a vortex separator; the system comprising a pressurized fluid generator and a vortex separator wherein:

the pressurized fluid generator includes a high pressure tank which connects to a fluid storage tank and a pressure indicator through a pressure booster pump, and at least an electric controlled switch is installed between the high pressure tank and the pressure booster pump and between the pressure booster pump and the fluid storage tank; a heating element and a temperature indicating controller are installed in the high pressure tank;

the vortex separator is connected to the pressurized fluid generator through transfer pipes; the vortex separator includes a vortex separating tank; the vortex separating tank has an outlet at a bottom side thereof; the outlet is connected to a plurality of collection bottles; a spindle is located in the vortex separating tank and is driven by a driving device so as to be moved vertically in the vortex separating tank; further, the spindle is installed with a penetrating fluid channel which is connected to a plurality of transfer pipes; each of the transfer pipes connected to the fluid channel is installed with at least a respective electric controlled switch; each of the transfer pipes is connected to a plurality of collection bottles; moreover, the vortex separating tank is further installed with a heating element and a temperature controller.

2. The integrated system for a pressurized fluid generator and vortex separator as claimed in claim 1, wherein the high pressure tank is connected to one of a co-solvent storage tank and a test agent through a transfer pump.

3. The integrated system for a pressurized fluid generator and vortex separator as claimed in claim 1, wherein the high pressure tank is installed with a safety releasing valve.

4. The integrated system for a pressurized fluid generator and vortex separator as claimed in claim 1, wherein the vortex separating tank is installed with a safety release valve.

5. The integrated system for a pressurized fluid generator and vortex separator as claimed in claim 1, wherein each of the transfer pipes is installed with a plurality of configurable pressure control valves, flow control valves, and flow meters.

* * * * *